(12) United States Patent
Tachauer et al.

(10) Patent No.: US 7,807,007 B2
(45) Date of Patent: Oct. 5, 2010

(54) MOLDING TOUCH FASTENER ELEMENTS

(75) Inventors: Ernesto S. Tachauer, Bedford, NH (US); Peter Iannazzi, Hampstead, NH (US); Christopher M. Gallant, Nottingham, NH (US); Mark A. Clarner, Concord, NH (US)

(73) Assignee: Velcro Industries B.V., Curacao (AN)

( * ) Notice: Subject to any disclaimer, the term of this patent is extended or adjusted under 35 U.S.C. 154(b) by 0 days.

(21) Appl. No.: 12/338,289

(22) Filed: Dec. 18, 2008

(65) Prior Publication Data

US 2009/0095411 A1    Apr. 16, 2009

Related U.S. Application Data

(62) Division of application No. 11/389,478, filed on Mar. 23, 2006, now abandoned.

(60) Provisional application No. 60/664,405, filed on Mar. 23, 2005.

(51) Int. Cl.
*B32B 38/10* (2006.01)
*B32B 27/00* (2006.01)
*B29C 47/06* (2006.01)

(52) U.S. Cl. .................. 156/247; 156/242; 156/244.11; 264/173.16; 264/173.1; 264/172.19

(58) Field of Classification Search ............ 264/172.19, 264/173.1, 173.16, 173.17, 167, 177.17; 425/402, 403; 156/247; 24/442–453; *B29D 11/00*; *B24D 11/00*
See application file for complete search history.

(56) References Cited

U.S. PATENT DOCUMENTS

| | | | |
|---|---|---|---|
| 4,078,340 A * | 3/1978 | Klecker et al. ................ | 51/295 |
| 4,872,243 A | 10/1989 | Fischer | |
| 5,212,853 A | 5/1993 | Kaneko | |
| 5,250,253 A | 10/1993 | Battrell et al. | |
| 5,312,456 A * | 5/1994 | Reed et al. ................... | 411/456 |
| 5,460,769 A | 10/1995 | Kaneko | |
| 5,591,146 A | 1/1997 | Hasse et al. | |

(Continued)

FOREIGN PATENT DOCUMENTS

DE    1944313    3/1971

(Continued)

OTHER PUBLICATIONS

Rosato, D.V., D.V. Rosato, and M.G. Rosato, Injection Molding Handbook (3rd Edition), Spring-Verlag, 2000, pp. 740-743.*

(Continued)

*Primary Examiner*—Richard Crispino
*Assistant Examiner*—William P Bell
(74) *Attorney, Agent, or Firm*—Fish & Richardson P.C.

(57) ABSTRACT

Methods of forming a sheet-form product can include: providing a forming surface having a multiplicity of inwardly extending forming cavities; forming a multi-layer sheet in the interior of which is a parting surface defined by materials of limited compatibility, material of the sheet lying on each side of the parting surface having peelable tensile strength; pressing the multi-layer sheet against the forming surface to cause the multi-layer sheet to substantially conform to and fill the cavities; and peeling the multi-layer sheet apart at the parting surface, whereby material directly engaging the forming surface defines a sheet-form member having a multiplicity of hollow formations.

27 Claims, 15 Drawing Sheets

U.S. PATENT DOCUMENTS

| | | |
|---|---|---|
| 5,679,302 A * | 10/1997 | Miller et al. ............ 264/167 |
| 5,769,832 A | 6/1998 | Hasse et al. |
| 5,797,170 A | 8/1998 | Akeno |
| 5,945,193 A | 8/1999 | Pollard et al. |
| 6,106,922 A | 8/2000 | Cejka et al. |
| 6,132,755 A | 10/2000 | Eicher et al. |
| 6,180,205 B1 | 1/2001 | Tachauer et al. |
| 6,224,807 B1 | 5/2001 | Clune |
| 6,303,062 B1 | 10/2001 | Aamodt et al. |
| 6,312,612 B1 | 11/2001 | Sherman et al. |
| 6,363,587 B1 | 4/2002 | Richter et al. |
| 6,451,240 B1 | 9/2002 | Sherman et al. |
| 6,470,540 B2 | 10/2002 | Aamodt et al. |
| 6,484,371 B1 | 11/2002 | Romanko et al. |
| 6,489,003 B1 | 12/2002 | Levitt et al. |
| 6,610,382 B1 | 8/2003 | Kobe et al. |
| 6,617,020 B2 | 9/2003 | Zhou et al. |
| 6,635,212 B1 | 10/2003 | Melbye et al. |
| 2004/0088835 A1 | 5/2004 | Tachauer et al. |
| 2004/0222551 A1 | 11/2004 | Provost et al. |

FOREIGN PATENT DOCUMENTS

| | | |
|---|---|---|
| JP | 2255103 | 10/1990 |
| WO | WO 99/17631 | 4/1999 |
| WO | WO 2005/018879 | 3/2005 |

OTHER PUBLICATIONS

Xie, Fei, "Second Office Action", Chinese Patent Application No. 20060008107.4, issued on Sep. 18, 2009 (12 pages).

* cited by examiner

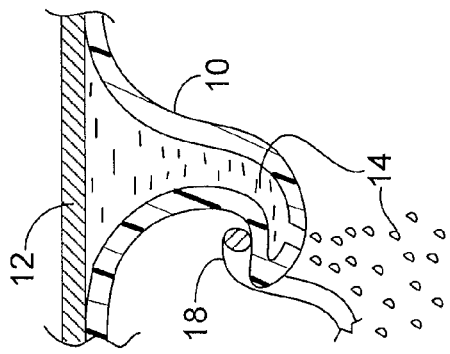
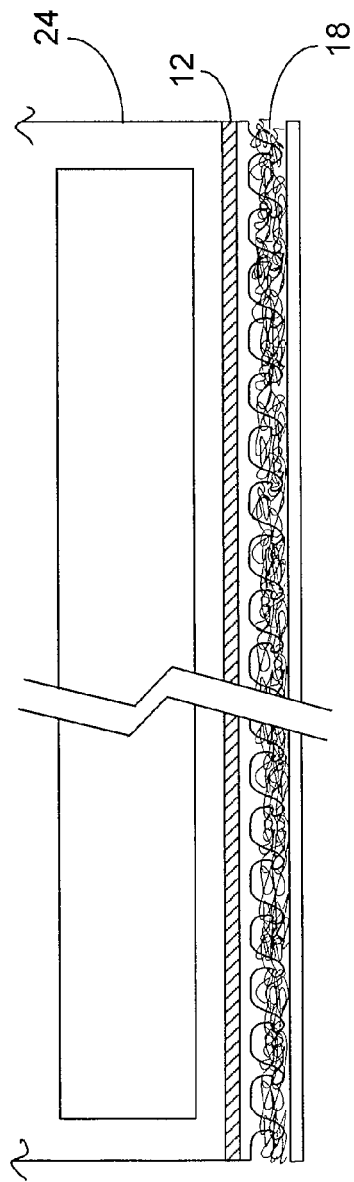
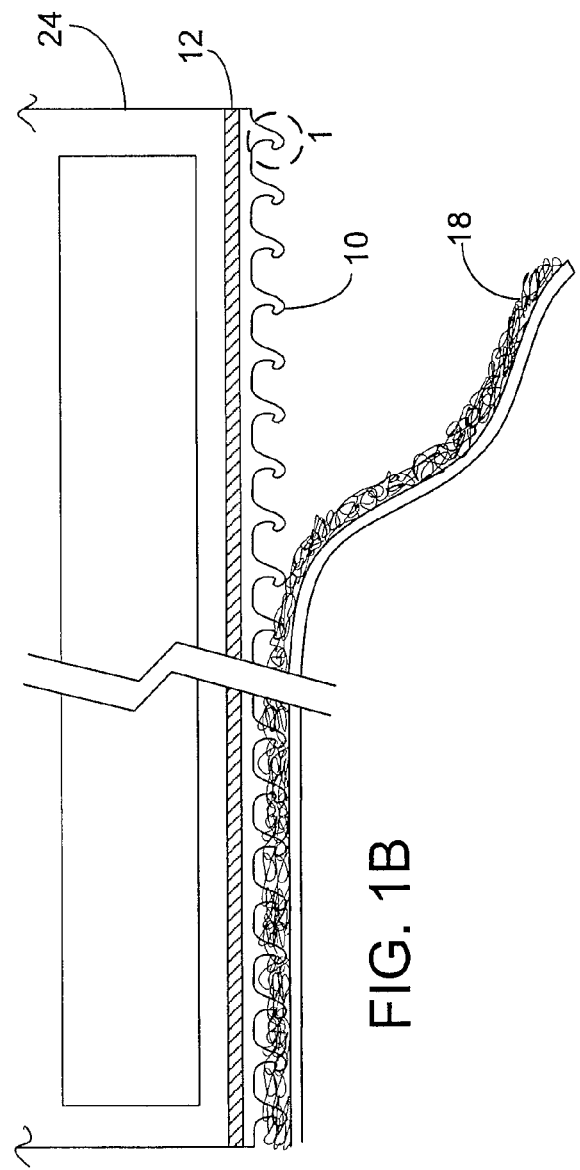
FIG. 1
FIG. 1A
FIG. 1B

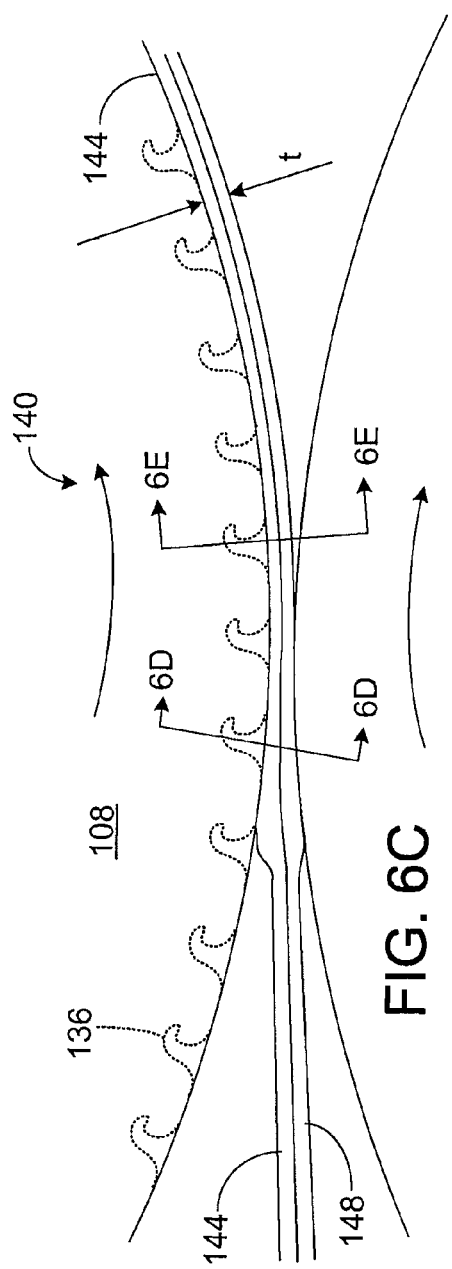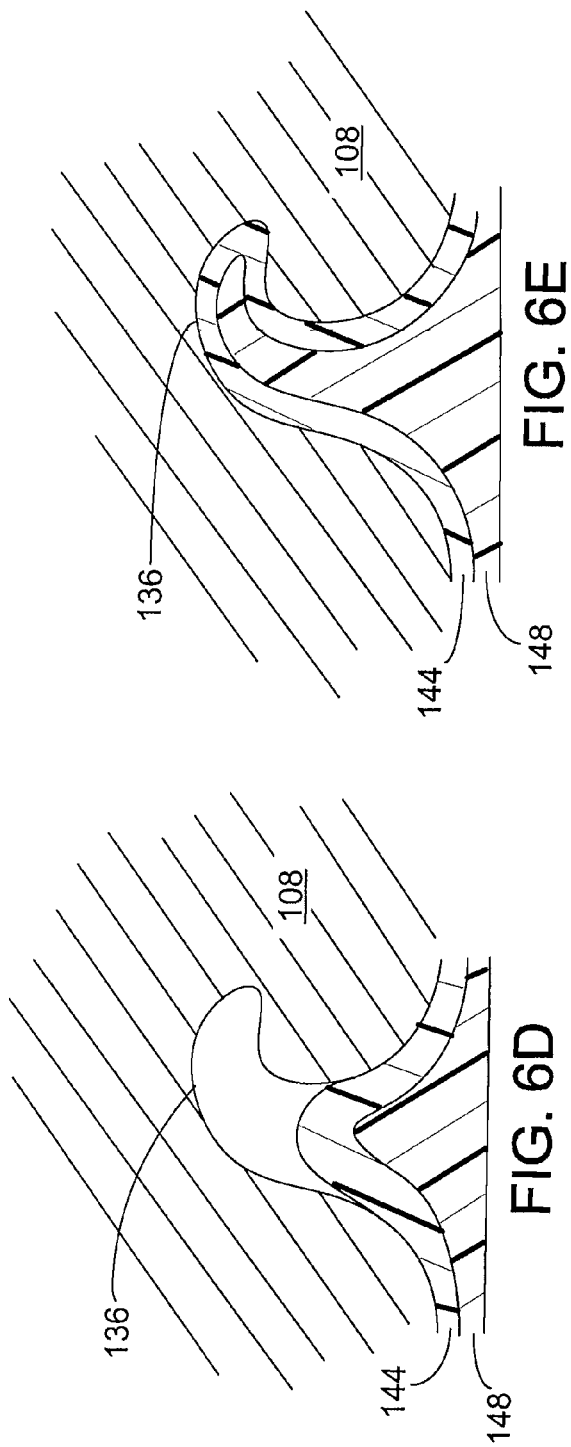

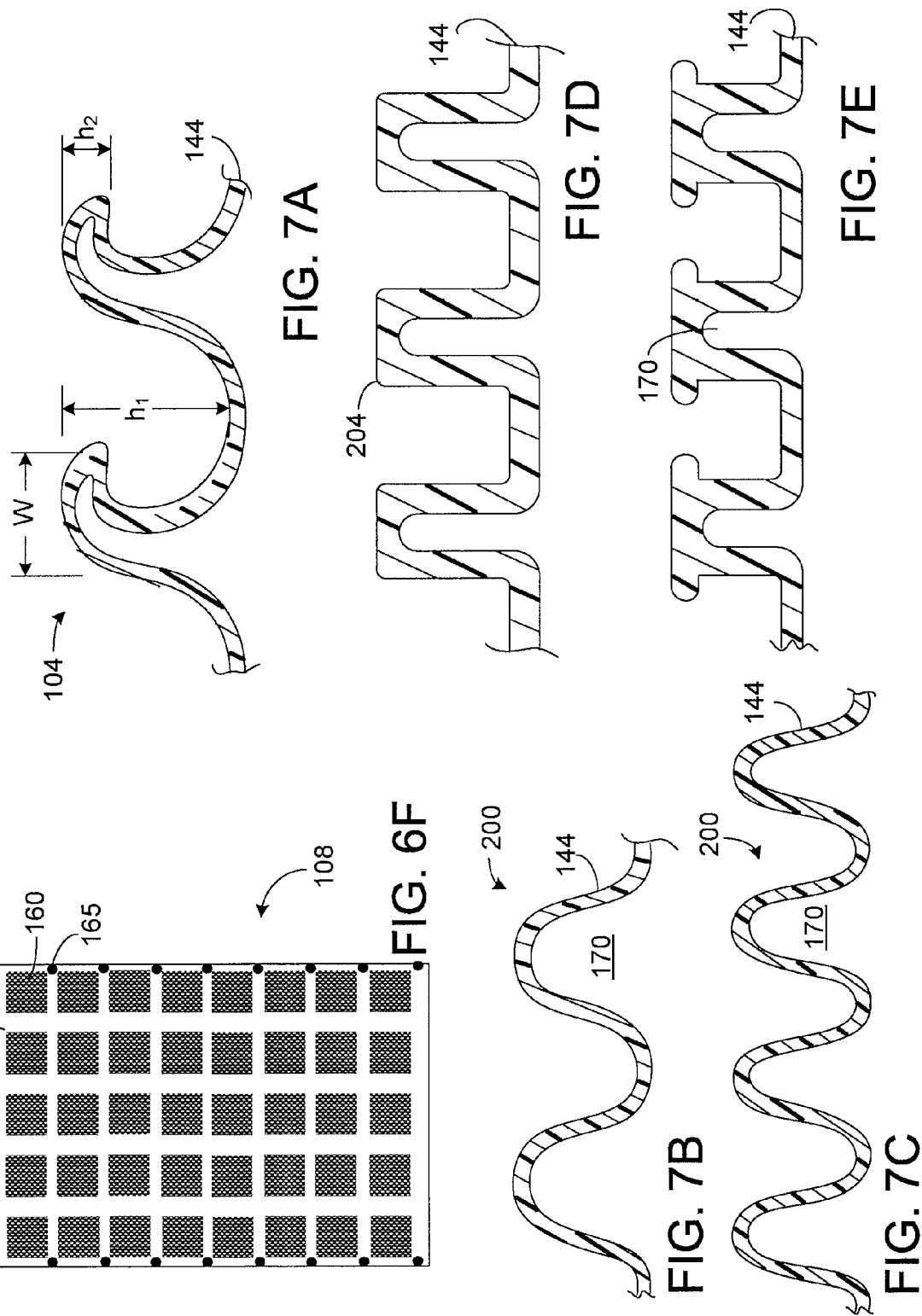

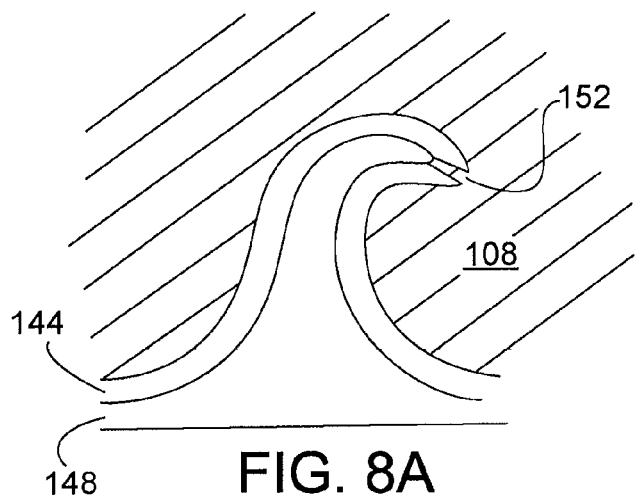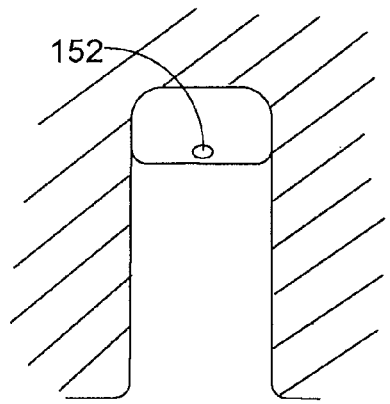
FIG. 8A          FIG. 8B
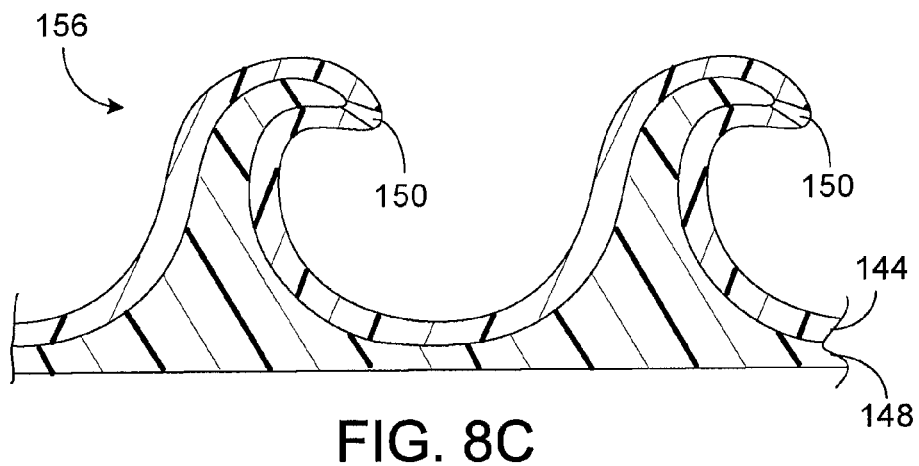
FIG. 8C
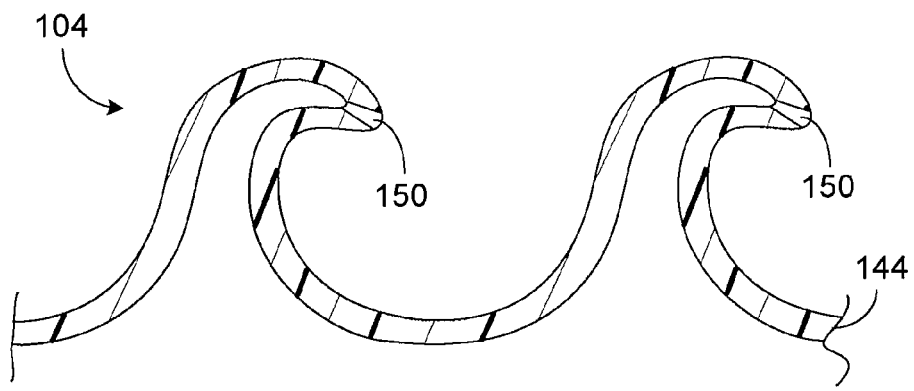
FIG. 8D

MOLDING TOUCH FASTENER ELEMENTS

CROSS-REFERENCE TO RELATED APPLICATIONS

This application is a divisional of U.S. patent application Ser. No. 11/389,478, filed Mar. 23, 2006, now abandoned which claims priority to U.S. Provisional Application No. 60/664,405, filed Mar. 23, 2005. The disclosure of each prior application is incorporated herein by reference.

TECHNICAL FIELD

This description relates to molding touch fastener elements, such as hooks for hook and loop fastening.

BACKGROUND

Touch fastener elements are molded in arrays for loop engagement. Many such fastener elements are very small, such as less than 0.5 millimeter in height, and are molded integrally with a flexible, sheet-form base. Some touch fastener elements are hook-shaped, and some are mushroom-shaped. Male touch fastener elements are shaped for releasable engagement with a field of loops or with another field of male touch fastener elements. Often the available fastener element shapes are limited by the molding method. For example, some shapes cannot be molded in closed cavities, as the molded elements cannot be pulled from the cavities without damaging the engageable heads. Furthermore, the fineness of particular features is limited by resin flow properties. Better fastener element formation methods are desired, as well as improved touch fasteners.

SUMMARY

According to one aspect, a product includes a base layer and a multiplicity of protruding hollow formations, the protruding formations unitarily formed with and extending upward from an upper surface of the base layer, the hollow formations and base layer formed of thermoplastic applied under pressure against a forming surface having forming cavities and the base layer having a back surface including interior surfaces of the hollow formations comprising a parting surface from which a second thermoplastic filling the hollow formations has been peeled. Embodiments of this aspect can include one or more of the following features.

The protruding formations can be elements of fastener formations. In some embodiments, the fastener elements are loop engageable formations that can be molded hooks. In other embodiments, the fastener elements are cylindrical hollow stems that can have post-formed distal ends. Alternatively, the protruding formations have sinusoidally curved upper surfaces (which can provide a skin-friendly texture), are cylindrical hollow stems (which can allow for easy removal from mold cavities), or are cones (which can provide a shape that is easy to truncate).

The protruding formations can have a height above the base layer of less than about 0.500 inches. In important cases, as where the projections form loop-engageable fasteners, the protruding formations have a height above the base layer of less than about 0.100 inches, but greater than about 0.005 inch. The protruding formations can have a height above the base layer of less than about 0.030 inches.

The product also can include a flowable substance filling the hollow formations. In some embodiments, the flowable substance is a liquid and, in other embodiments, the flowable substance is a fine powder.

The product also includes a backing layer at least part of which forms a bond to a surface of the base layer so that the multiplicity of protruding formations cooperate with the backing layer to define a multiplicity of substantially enclosed chambers containing the flowable substance. In some embodiments, the bond between the base and backing layer substantially seals individual chambers so that movement of the flowable substance out of the individually sealed chambers through the base layer is limited by the backing layer. In other embodiments, the bond between the base and backing layers substantially seals groups of the chambers, individual chambers within the groups of chambers remaining in fluid communication with each other while movement of the flowable substance out of the groups of chambers is limited by the backing layer.

In some embodiments, at least 10 percent of the protruding formations also define an upper opening for dispensing the flowable substance. The opening can be sized such that surface tension and viscosity substantially retain the flowable substance within the chambers until the protruding formations deform in response to applied pressure. The product can also include a sealing strip covering the upper openings, the sealing strip removable to dispense the flowable substance through the upper openings. Alternatively, the protruding formations can contain discrete areas whose structural strength is weaker than the structural strength of other areas of the protruding element.

In some embodiments, the flowable substance comprises a component that volatilizes when exposed to the atmosphere. Dispersion of the volatile component can release a generally aesthetically-pleasing odor. In these embodiments, the thermoplastic forming the hollow formations can be chosen from thermoplastics whose permeability allows dispersion of the volatile component through the thermoplastic.

In some applications, the product includes a disposable, absorbent undergarment wherein the base layer, hollow formations, flowable substance, and backing layer are attached to the disposable, absorbent undergarment. In other applications, the product includes a container liner portion wherein the base layer, hollow formations, flowable substance, and backing layer are attached to the container liner portion. In still other applications, the product includes a sampler portion wherein the base layer, hollow formations, flowable substance, and backing layer are attached to the sampler portion with a sealing layer covering the first portion and limiting movement of the flowable substance out of the first portion, the sealing layer removable to dispense the flowable substance.

In some embodiments with a flowable substance, the flowable substance includes a medicament appropriate for topical application. The medicament can include an antibiotic or an analgesic. The flowable substance can include components that reduce transmission of ultraviolet radiation. The flowable substance can include components that repel insects.

In another aspect, a method of forming a sheet-form product includes providing a forming surface having a multiplicity of inwardly extending forming cavities and forming a multi-layer sheet in the interior of which is a parting surface defined by materials of limited compatibility, material of the sheet lying on each side of the parting surface having peelable tensile strength. The multi-layer sheet is pressed against the forming surface to cause the multi-layer sheet to substantially conform to and fill the cavities; and the multi-layer sheet is peeled apart at the parting surface, whereby material directly engaging the forming surface defines a sheet-form member having a multiplicity of hollow formations. Embodiments of this aspect can include one or more of the following features.

The forming cavities can define at least stems for fastener elements. The forming cavities can define cylindrical formations or loop engageable formations such as molded hooks. Alternatively, the forming cavities can define sinusoidally curved surfaces, cones, or cylindrical hollow stems.

The forming cavities can extend into the mold roll a distance less than about 0.100 inches. The forming cavities can extend into the mold roll a distance less than about 0.030 inches.

Forming a multi-layer sheet can include continuously introducing a first molten thermoplastic and a second molten thermoplastic into a gap defined adjacent to the forming surface. Continuously introducing can include extruding the molten thermoplastics as a molten sheet from a co-extruder die.

In some embodiments, the method also includes forming a dispensing hole in the hollow formations. Forming a dispensing hole can include laser radiating the hollow formations to burn through the sheet-form member. Alternatively, forming a dispensing hole can include mechanically piercing the hollow formations.

In some embodiments, mold pins extend into the forming cavities from a body of the forming surface.

In some embodiments, the method also includes weakening a discrete area of the hollow formations. Weakening can include laser radiating the hollow formations for a period of time chosen to decrease the structural strength of a discrete area of the hollow formations without burning through the sheet-form member.

The method can also include filling the hollow formations with a flowable substance. In some embodiments, the method also includes, after filling, bonding a backing layer to the sheet-form member to form a multiplicity of substantially enclosed chambers. In some embodiments, the flowable substance includes a component that volatilizes when exposed to the atmosphere. Dispersion of the volatile component can release a generally aesthetically-pleasing odor. The sheet-form member can be formed of a thermoplastic chosen from thermoplastics whose permeability allows dispersion of the volatile component through the thermoplastic. In some embodiments, the flowable substance includes a medicament appropriate for topical application. The medicament can include an antibiotic and/or an analgesic. In some embodiments, the flowable substance comprises components that reduce transmission of ultraviolet radiation. In some embodiments, the flowable substance comprises components that repel insects.

In another aspect, a hook component of a hook and loop fastener system includes a field of loop-engageable hollow elements projecting from a base layer. It also includes a flowable substance within the hollow elements; and a dispensing feature enabling dispensing of the flowable substance in response to deformation of the loop-engageable elements.

In some embodiments, a backing material and the hollow loop-engageable elements define cavities containing the flowable substance.

The hollow loop-engageable elements can include hooks having loop-engageable heads.

In some embodiments, the hollow loop-engageable elements are deformable in response to stress between about 0.1 and 2 pounds per inch width of the product. The hollow loop-engageable elements can be deformable in response to disengagement of the hook component from a mating fastener component. Alternatively, the stress can be applied by direct pressure applied by a user pressing on the elements.

The hollow loop-engageable elements can dispense the flowable substance when deformed.

In an aspect, a method of forming a sheet form product includes forming a multi-layer sheet having a first layer forming a first broad surface of the multi-layer sheet; pressing the multi-layer sheet against a forming surface with the first layer contacting the forming surface such that the multi-layer sheet substantially conforms to and fills a multiplicity of inwardly extending forming cavities in the forming surface; removing the multi-layer sheet from the forming surface; removing the first layer from remaining portions of the multi-layer sheet, the remaining portions of the multi-layer sheet defining a member having stems of fastener elements integrally molded with and extending from a sheet-form base.

In some embodiments, the first layer is interposed between the remaining portions of the multi-layer sheet and the forming surface when the multi-layer sheet is pressed against the forming surface. The remaining portions can include additives. In some instances, the additives include materials, such as titanium dioxide or calcium carbonate, that increase the rate of accumulation of contaminating material on the surfaces the resin and additives contact and the method further comprises sizing a thickness of the first layer to limit contact between the forming surface and the remaining portions. In some instances, the additives comprise materials that increase abrasive characteristics of the remaining portions and the method farther comprises sizing a thickness of the first layer to reduce wear on the forming surface from the remaining portions.

In some embodiments, the method also includes sizing a thickness of the first layer based on sizes of irregularities in the forming surface.

In some embodiments, the method also includes selecting materials for the first layer that have a first flexural modulus and materials for the remaining portions that have a second flexural modulus such that the second flexural modulus is greater than the first flexural modulus. In some instances, the second flexural modulus is greater than 300,000 pounds per square inch (e.g., greater than 500,000 pounds per square inch or greater than 750,000 pounds per square inch). In some instances, removing the multi-layer sheet from the forming surface comprises compressing the first layer between the forming surface and remaining portions. In some instances, the method also includes forcing the remaining portions through the first layer.

Hollow elements as described herein can be used in a variety of settings to store and dispense flowable substances such as fragrances, medicines, inks, and insect repellents. Such dispensers can be used in a security device in conjunction with a seal and configured to release fluids when the seal is broken. Such dispensers can also be used to store substances such as lotions, cleansers, and medicines in portable containers for convenient use while, for example, traveling in a car or airplane. Hollow elements can be configured with smooth surfaces for skin-friendliness. Hollow elements can also be configured as fastener elements such as molded hooks. Hollow fastener elements can be used as both dispensers and fastener elements when filled with a suitable fluid (e.g., in a security device application). Hollow fastener elements (e.g., molded hollow hooks with empty central voids) are anticipated to provide aggressive fastener characteristics and improved flexibility relative to similar hooks with a solid core. The methods of producing hollow elements (e.g., roll molding) described herein provide an efficient technique producing such fastener elements and dispensers using, for example, the upper portions of multiple-layer substrates and discarding and/or recycling the lower portions of the multiple-layer substrates.

In one aspect, a method of forming fastener elements includes pressing moldable material against a forming surface having a multiplicity of inwardly extending forming cavities using a surface with protrusions aligned with the cavities. The moldable material is pressed against the forming surface to cause the moldable material to substantially conform to and fill the cavities. The moldable material is removed from the forming surface.

The use of multiple-layer substrates can also provide increase in efficiency and improved product quality for molding processes. A sacrificial layer adjacent the molding surface can make in more feasible to include additives to the remainder of the substrate that might otherwise damage the molding surface. For example, a sacrificial layer can used to separate portions of substrate containing coloring agents (which can increase contamination of the molding surface) or containing metal pieces (which can increase wear damage to the molding surface) from the molding surface. In addition, constraints on producing mold surface limits the minimum size of molded features (e.g., molded hook heights, molded hook tip configurations). However, use of a sacrificial layer (e.g., effectively the use of resin as part of the tooling) can provide an approach for molding small fine features. In both of these approach, the sacrificial layer can subsequently be removed from the remainder of the substrate as part of the process of forming a fastener product.

The details of one or more embodiments are set forth in the accompanying drawings and the description below. Other features, objects, and advantages will be apparent from the description and drawings, and from the claims.

DESCRIPTION OF DRAWINGS

FIG. 1 is a highly magnified vertical cross-section view of a hollow fastener hook element for hook and loop fastening.

FIGS. 1A and 1B are schematic side magnified views of an ink-filled tamper evident fastener product incorporating the hollow hook of FIG. 1, respectively, before and after disengagement of the fastening.

FIG. 6C is side view of a two-layer sheet of resins entering the calender nip formed with a mold roll as shown in FIGS. 6A and 6B, with mold cavities indicated diagrammatically.

FIGS. 6D and 6E are cross-sections of resins entering mold cavities at progressive stages as indicated in FIG. 6C.

FIG. 6F is a developed plan view of the surface of the mold roll shown in FIGS. 6A and 6B.

FIGS. 7A through 7E are cross-sections of various hollow element embodiments.

FIGS. 8A and 8B are cross-section views of a mold with a protruding pin taken in, respectively, the cross-machine and machine directions.

FIGS. 8C and 8D are cross-section views of molded hooks produced by the mold of FIGS. 8A and 8B before and after the second resin is removed.

Like reference symbols in the various drawings indicate like elements.

DETAILED DESCRIPTION

Figure 2:
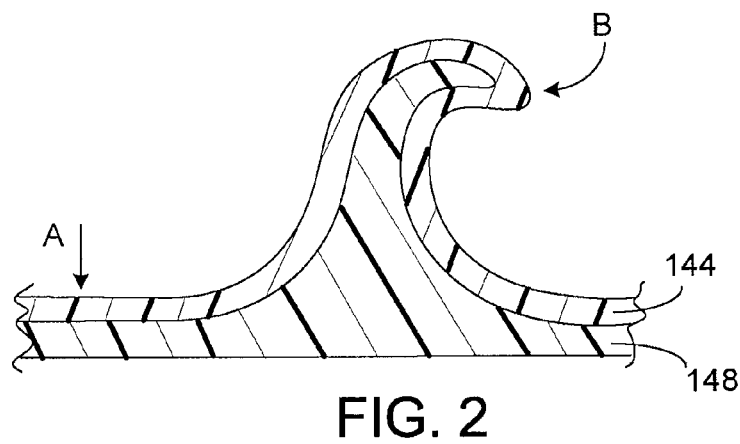
FIG. 2 is a cross-section of a sheet-form product molded of two adjoined resin layers.

Hollow hooks are usable in a wide variety of applications. For example, referring to FIGS. 1, 1A, and 1B, a hollow loop-engageable fastener hook 10 has its internal hollow volume sealed with backing material 12 to contain ink 14. The ink is provided to produce a visual signal when the hook is disturbed. As shown, hooks 10 engage loops 18 a fastener loop material to seal bag 24. The action of opening bag 24 causes release of the ink to provide a visual indication that the fastening has been opened, see FIGS. 1 and 1B. For this purpose, hooks 10 are made of a flexible material so that stress, exerted on the hooks 10 as the hooks bend to release the loop 18, compresses the volume within the hooks 10 to dispense the ink 14 through a suitable aperture.

Figure 3:
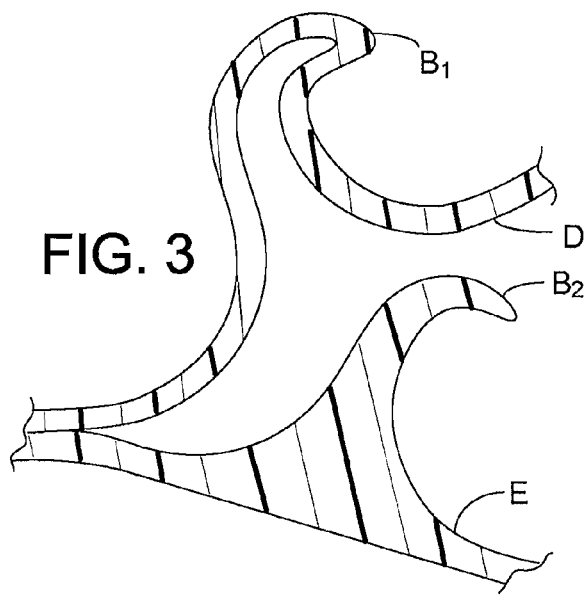
FIG. 3 is a similar cross-section as the resin layers are peeled apart.

Referring to FIGS. 2 and 3, a system and method for forming the hook depend on selection of formable thermoplastic resins 144 and 148, which, though suitable for being provided as a sheet A of adjacent joined layers, have, or are treated or formulated to have, limited compatibility. The term "limited compatibility" means that the adjacent resins, (1) under face-to-face joined conditions, have sufficient compatibility to form a coherent combined sheet A, in which the resins of the adjacent layers do not substantially diffuse into one another or otherwise form a tenacious bond, but do have sufficient adherence to remain united during passage through a forming process to jointly form projections, such as hooks B, standing from the sheet and (2) under formed conditions, have such limited adherence as to permit separation at parting surface by peeling action, see FIG. 3. Furthermore these two separable resins in the form of layers, or, these resin layers in combination with other resin layers tenaciously joined to their oppositely directed sides, must have peelable tensile strength. The term "peelable tensile strength" means that the separable resins, or separable resin groups, in practical thicknesses, have sufficient strength to remain intact under peeling tension, such that respective separable sheets D, E and interfitted small projections from these sheets, such as the hook form elements $B_1$ and $B_2$, are separable as coherent units by peeling, thus producing a sheet-form product, F, see FIG. 4, having a field of hollow projections $B_1$, and an exposed parting surface. In preferred cases, referring to FIG. 5, the starting sheet A of joined layers is formed by extrusion of melted resin in which the resins do not substantially diffuse into one another and the projections are formed by molding the sheet-form resins while at a moldable temperature.

Figure 6A:
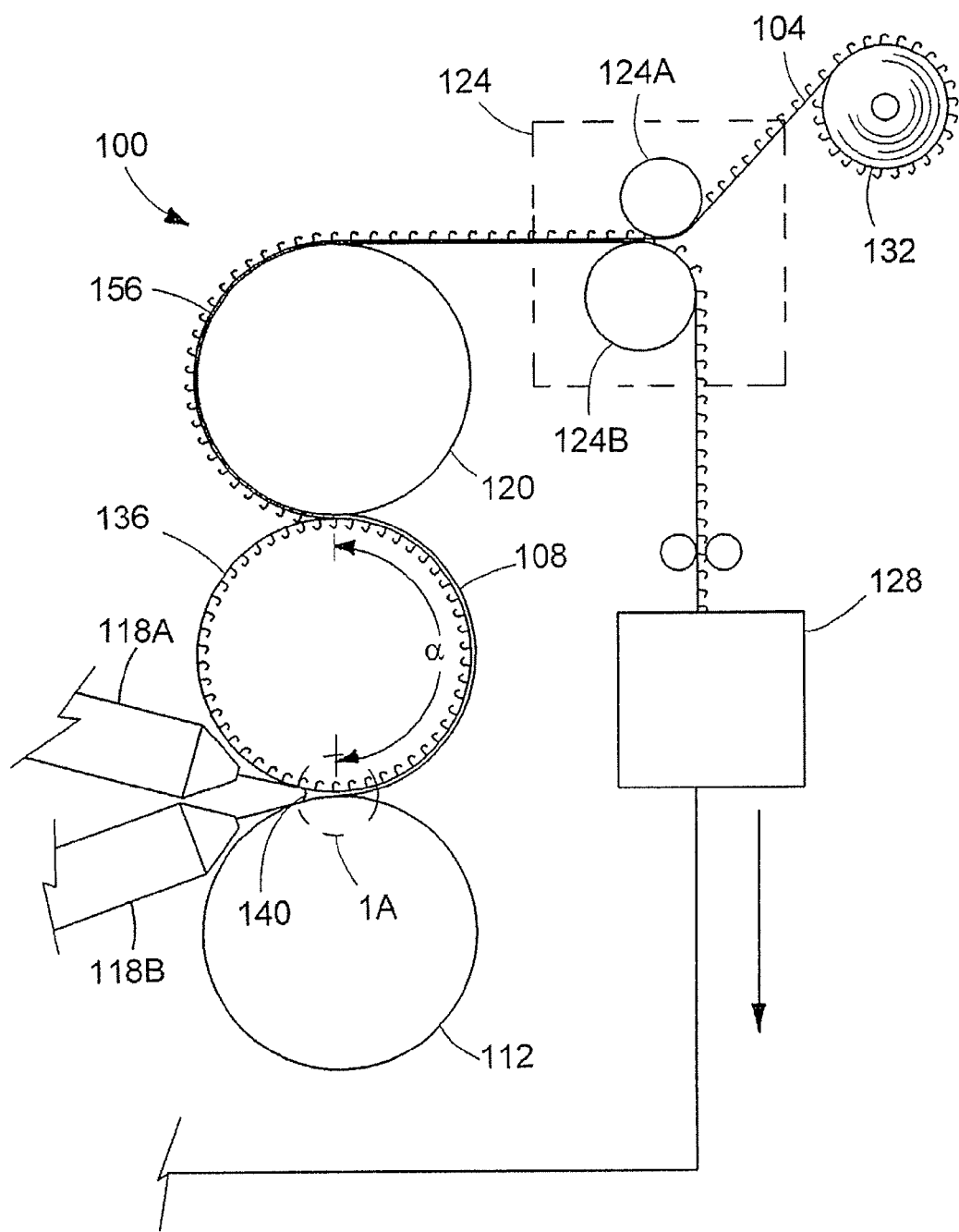
FIG. 6A is a schematic diagram of a system for producing small hollow elements on a web product.
Figure 6B:
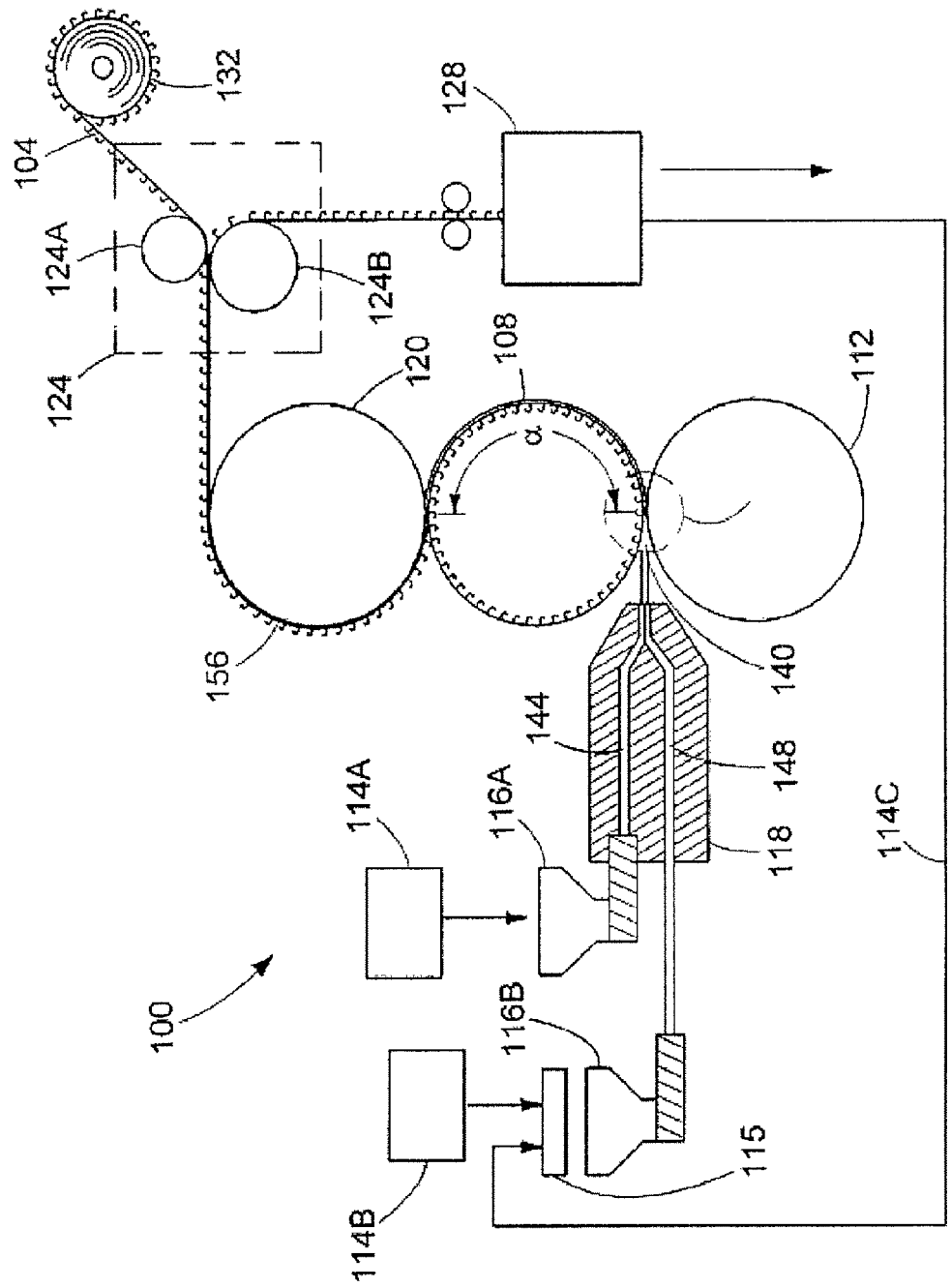
FIG. 6B is a schematic diagram similar to FIG. 6A of an alternate embodiment.

Referring to FIG. 6A, manufacturing system 100 is employed to produce a thermoplastic web product carrying a field of small hollow formations 104 on its surface. In a preferred form, the system employs roll molding apparatus of the general type shown in U.S. Pat. No. 4,872,243 issued to Fischer. In the present case, the nip is fed from two extruder dies 118A and 118B. Referring to FIG. 6B, in an alternate embodiment, the nip of the molding apparatus is fed by a co-extrusion die 118 in the general arrangement illustrated in U.S. Pat. No. 5,945,193 issued to Pollard et al., the details of each of which being hereby incorporated by reference.

Referring to FIGS. 6A and 6B, the manufacturing system 100 includes a roll molding apparatus comprising temperature-controlled cylindrical mold roll 108, temperature-controlled cylindrical pressure roll 112, and a suitable extrusion arrangement. In FIG. 6B, for instance, co-extruder die 118 fed by two extruders 116A, B. The extruders 116A, B receive resin from respective feedboxes 114A, B, preferably flow from the latter feed box mixing with reclaim flow 114C in mixer 115. Mold roll 108 is followed by take-off roll 120, separator station 124, take-up roll 132, and reclaim grinder 128. Mold roll 108 has a field of small mold cavities 136 in its peripheral surface, for example mold cavities shaped to form projections of heights in the range between about 0.005 and 0.100 inch. Mold roll 108 and pressure roll 112 are counter-rotating rolls that define nip 140.

In operation, flows of first and second resins from feedboxes 114A, B, in many advantageous cases, the latter mixing with a predominant flow of reclaim resin 114C from reclaim grinder 128, are introduced to extruders 116A, B. Extruders 116A, B shear and melt resins 144, 148 and introduce the melted resins under pressure into co-extrusion die 118. The co-extrusion die 118 extrudes molten resin in sheet-form comprised of two adhered layers 144, 148, as shown in FIG. 6C. The molten sheet is led into calender nip 140. The motion of the counter-rotating surfaces draws the molten sheet into nip 140. The pressure of nip 140 forces the two layer molten resin sheet into mold cavities 136. The final thickness t of a two layer base sheet is determined by the spacing of the roll surfaces at the calender nip and is typically about 0.002 to 0.010 inch. The layer thicknesses and hook dimensions are exaggerated for clarity of illustration and are not to scale.

As diagrammatically shown in the sequence of FIGS. 6D and 6E, during passage through the nip 140, the pressure of the nip forces the face-to-face resins 144, 148 progressively into mold cavities 136. A portion of the first resin 144, defining the upper layer of the sheet, flows into each exposed mold cavity against the surfaces bounding the cavity. The outer portion of this resin thus assumes the cavity configuration while the body of this resin remains integral with adjacent portions of the layer from which it originates. A corresponding portion of the lower resin layer moves with the upper resin to occupy the center region of each mold cavity while it too remains integral with adjacent portions of its layer. Based on selection of the resins to have limited compatibility and peelable tensile strength, the two parts of each projection along with their respective base layers, when solidified, are separable by peeling.

Following nip 140, the thermoplastic continues on the surface of the rotating temperature controlled (cooled) mold roll through arc α until the resin is sufficiently solidified to enable removal from the mold roll. The web is led from mold roll 108, about a small takeoff roll, not shown, to roll 120 thence to separator station 124 by applied tension. (Though, in some embodiments, it can be advantageous to remove the second resin at a later stage).

At separator station 124, the upper layer, carrying the mold-shaped outer portions of the projections, is peeled from the lower layer carrying the central portions of the projections, producing two separated webs. This is accomplished by leading the separating layers about opposed rolls, 124 A,B under tension produced by downstream pulling arrangements, not shown. After peeling apart, the upper base layer with its hollow projections 104 proceeds to take-up roll 132, and the lower base layer with its projections is directed to reclaim grinder 128.

In alternate embodiments of the system without a separator station, the web is initially stored on take-up roll 132 with the two layers still attached to each other to be separated later, for instance as the material proceeds into a filling system.

Thus, based upon selection of resins 144, 148 to have limited compatibility and peelable tensile strength and use of suitable operating conditions, the integrity of each resin layer is preserved to enable molding and subsequent peeling apart while having sufficient compatibility that the layers adhere to one another and flow as a unit into the molding cavities 136. First layer, comprising a field of hollow projections 104 extending from the upper base layer has numerous uses, for instance in the dispensing of liquid or powdery fluids or providing desirable, crushable properties, while being capable of performing other functions as well, such as fastening functions.

In general, the weight ratio of first resin 144 to second resin 148 is selected based on the shape of the mold cavities, the desired layer thickness of first resin 144 in the final product, and any desired further functionality. For many preferred embodiments, appropriate weight ratios range between approximately 1 to 2 to approximately 2 to 1. In one example, when forming projections as loop-engageable fastener hooks, Pro-fax® SD242, a polypropylene, available from Basell Company was selected as first resin 144, and Affinity® PT1450, a polyolefin plastomer, available from the Dow Chemical Company was selected as second resin 148. A weight ratio of 1 to 1 was employed. In commercial production, 80% reclaim and 20% fresh resin may be used for the second resin although only fresh resin was used in this example. In this example, single screw extruders 116 A,B were operated with the SD 242 melt in the range of approximately 420 to 450 degrees F. and the Affinity® PT1450 melt in the range of approximately 390 to 420 degrees F. These conditions take into consideration resin characteristics such as the fact that SD 242 has higher melting point than Affinity® PT1450. Other process variables such as roll temperature and line speed were selected based upon the base layer thicknesses, size and shape of the projections, and weight ratios, using customary operator skills.

The distribution of mold cavities 136 in the peripheral surface of mold roll 108 determines the distribution of hollow elements 104. For example, the developed mold roll surface shown in FIG. 6F has groups 160 of mold cavities 136 separated by flat mold roll surface portions 164. This produces a product with islands of hollow elements 104 separated by plain regions of connecting material. As discussed below, such distribution patterns facilitate sealing of the volume defined by the hollow elements. Mold roll 108 in this example also has registration mold cavities 165 to produce registration features on the sheet of hollow hooks. In some methods of manufacturing fastener products, fillers (e.g., titanium dioxide ($TiO_2$) or calcium carbonate ($CaCO_3$)) are added to the resin from which hooks are manufactured in order to affect the color or other properties of the resulting fastener products. However, it has been observed that filled resins can contaminate tooling (e.g., cause buildup of material on mold roll 108) more quickly than non-filled resins. Tool contamination is undesirable as it can result in decreased hook performance, increased downtime for tools and machines, and increased manufacturing costs associated with chemical and personnel requirements for cleaning and rebuilding the tools. In some embodiments, methods similar to those described above can be used to reduce contamination of tooling. For example, referring again to FIG. 6E, a "clean" non-filled resin can be run in top layer 144 with a normal or highly filled resin run in bottom layer 148. This results in reduced tooling contamination, as filled resin layer 148 would never touch the tooling (e.g., mold cavity 136). Systems implementing such methods would differ from system 100 in that lower layer 148 (rather than or in addition to upper layer 144) would form at least part of a desired fastener product. Consequently, lower layer 148 would be collected and stored (e.g., wound onto a storage spool) rather collected and recycled.

Similarly, in some methods, upper layer 144 can be used to protect tooling surfaces from potentially abrasive additives in resin of lower layer 148. In some instances, it is desirable to include additives (e.g., glass, metal pieces, etc.) into resin to stiffen the resulting fastener formations and/or to create barbs and friction points for engaging loops. Such additives have the potential to cause wear damage to mold cavities 136. However, the additives can be included in bottom layer 148 and not in upper layer 144 such that the upper layer serves as a sacrificial layer which can reduce wear damage on mold cavities 136.

In some methods, upper layer 144 can be used to protect fastener products formed from lower layer 148 from the tooling surfaces (e.g., rather than or in addition to protecting the tooling surfaces from components of the resin forming the lower layer). Rough tooling surfaces (e.g., irregularities in tooling surfaces as small as 0.0001 inch) in mold cavities 136 can contribute to contamination, can cause difficulty in removal of formations (e.g., fastener hooks) from the mold cavities, and can result in loss of hook shape and functionality after removal from the mold cavities. Consequently, ring cutting and polishing processes are used to provide smooth mold cavities 136. The costs associated with the cutting and polishing processes can be reduced when the bottom layer 148 of hooks is the primary layer to be used as surface roughness issues may no longer be a problem. Upper layer 144 can provide a smooth surface that, when separated from the bottom layer 148, will leave the bottom layer in its desired shape.

Apparatus 100 is capable of producing small (i.e. height of less than about 0.050 inch) hollow elements 104. For example, the resins discussed above have been used to produce hollow loop-engageable fastener hooks 104 as shown in FIG. 7A with an overall height $h_1$ of approximately 0.023 inch, a crook height $h_2$ of approximately 0.005 inch, and width w of approximately 0.013. These exemplary hollow hooks 104 were formed with individual void volumes of approximately $1 \times 10^{-6}$ $inch^3$. As is apparent, the projections 104 shown in FIGS. 6A and 6B as well as the mold cavity outlines of FIG. 6C are not to scale but rather are shown to illustrate their location relative to mold roll 108 and other components of apparatus 100. Other element shapes, such as semi-spheres having diameter of 0.005 to 0.010 inch, can be produced by corresponding designs of mold cavities 136. For example, 176 as shown in FIGS. 7B and 7C, skin-friendly products are made of rounded dispensers 200 of first resin 144. Similarly, as shown in FIG. 7D, hollow stem dispensers 204 are produced by forming hollow stems in straight cylindrical mold cavities, in some cases by subjecting the distal ends of stems 204 to heat and pressure of a post-forming process, as by flame or radiant heating optimally followed by passing through a calender nip of a post-forming process, loop-engageable heads are formed, e.g. of mushroom or flat-top configuration, the latter shown in FIG. 7E.

As discussed above, second resin 148 is reclaimed and reused after being removed from hollow formations to reduce process costs. Due to gradual thermal degradation and mixing with first resin 144, it is necessary to replace second resin 148. It is presently anticipated that this will be accomplished by making the feed to extruder 116B approximately 80% reclaimed second resin 148 from grinder 128 and 20% fresh second resin 148. However, under different operating conditions, second resin 148 replacement will be performed using different ratios reclaimed to fresh resin or even on a batch basis, replacing all of the second resin from time to time.

For many embodiments adapted to dispensing fluids from the hollow volumes or otherwise having provision for communication between the hollow volumes and the exterior, upper openings 150 are formed in hollow elements 104. Referring to FIGS. 8A and 8B, in one embodiment, mold cavities are provided with mold pins 152 that are shaped to form upper openings 150. Mold pin 152 is dimensioned to extend from the body of mold roll 108 through first resin 144 into second resin 148. Referring to FIGS. 8C and 8D, when take-off roll 120 removes resins 144, 148 from the peripheral surface of mold roll 108 after solidification, molding apparatus 100 has formed two-resin hooks 156. After peeled separation of the layers, hollow hooks 104 remain with a hole 150 through a wall of each hook.

Figure 8H:
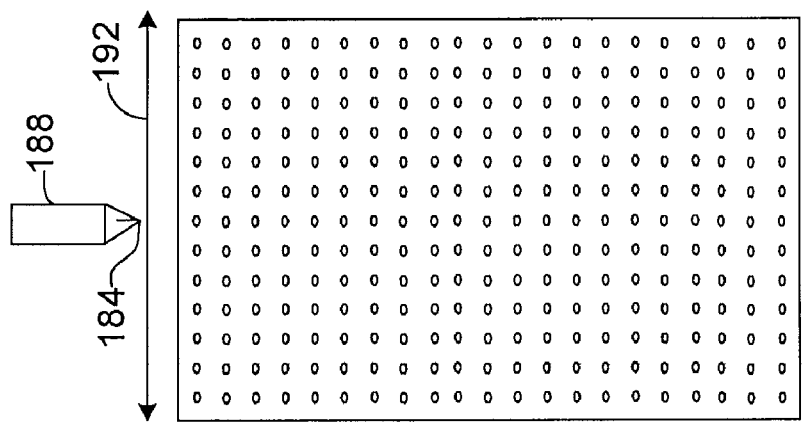
FIGS. 8F-8H are, respectively, a side view, a larger-scale side view, and a developed view of using a laser station for creating holes in conical hollow elements.
Figure 8E:
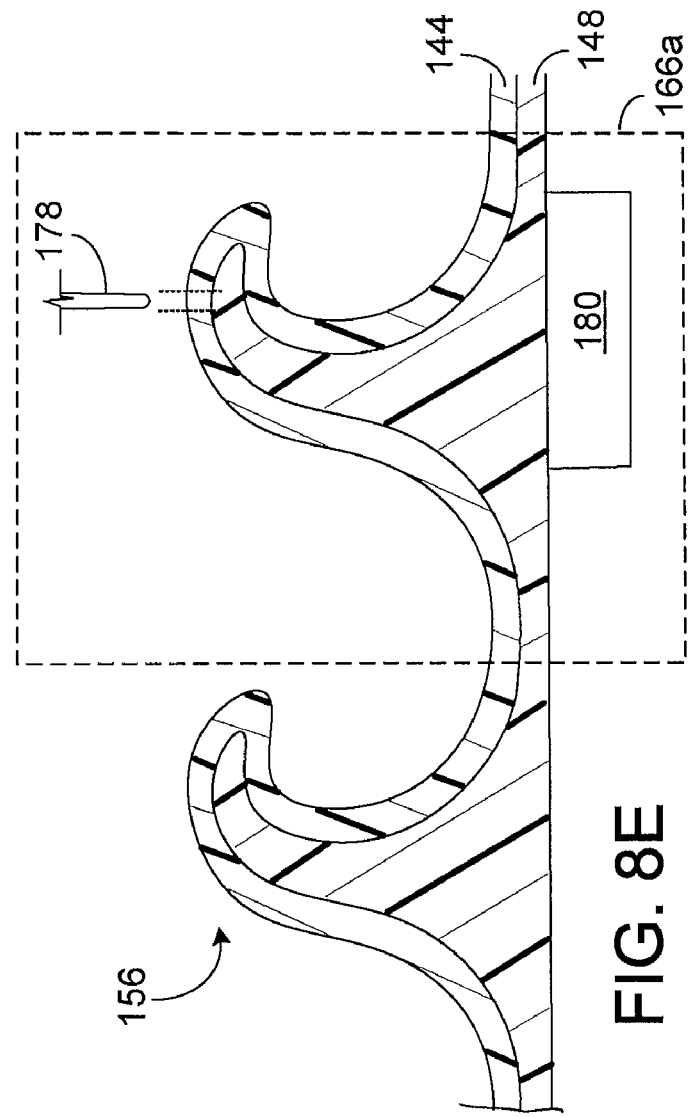
FIG. 8E is a cross-section of a mechanical piercing station for creating holes in hollow hooks.

In other embodiments, as illustrated in FIG. 8E, reciprocal piercing pins 178 are caused to pierce two-resin hooks 156 at mechanical piercing station 166a while the material is supported by support member 180. In certain embodiments of this aspect, mechanical piercing station 166a is located between takeoff roll 120 and stripping station 124, thus second resin 148 is present during the piercing action and provides interior support as pins 178 are driven through first resin 144. In one example, mold roll 108 includes mold cavities that mold registration features 165 on the web (FIG. 6F). These are engaged to provide positive registration between hooks and the piercing pins to ensure proper alignment during the operation. In other embodiments, other alignment systems are employed, examples being based on optical tracking of features or of marks provided on the web.

Figure 8F:
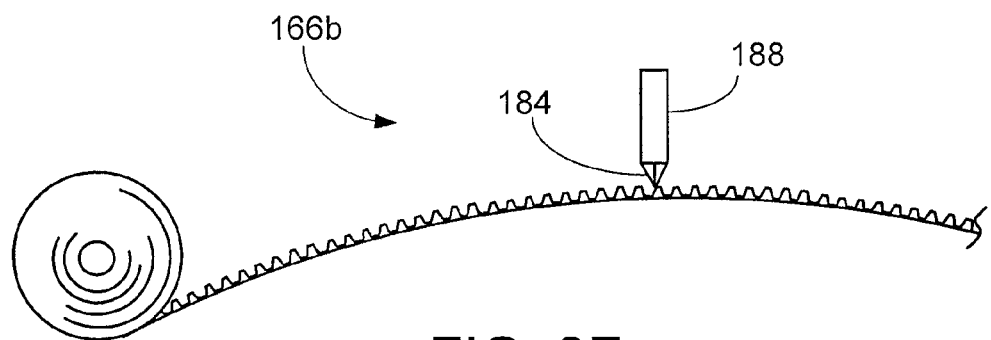
Figure 8G:
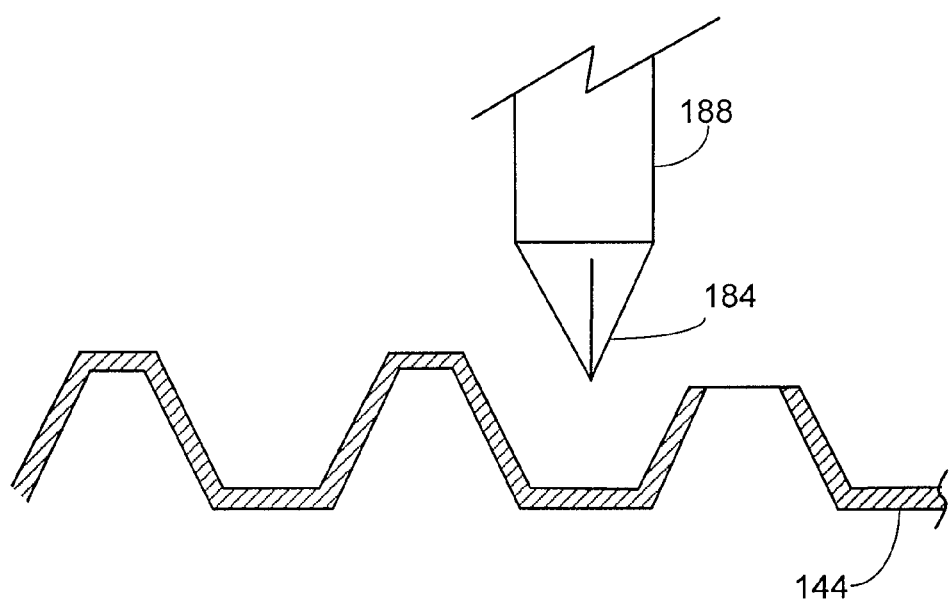

In other embodiments, as illustrated in FIGS. 8F-8H, a laser beam 184 burns holes through first resin 144. Optional laser station 166b is preferably located between stripping station 124 and take-up roll 132. Laser 184 or a suitable reflecting mirror is mounted on a translating member 188 to provide a side-to-side motion 192 sweeping the laser beam along rows of hollow elements. A registration system, such as one of those described above, is employed to assure alignment of the laser beam with the desired regions for laser action. In a further embodiment, the laser energy is controlled to selectively weaken discrete areas of the hollow elements rather than creating complete holes through first resin 144. The remaining resin membrane preserves fluid tightness while enabling opening of passages by a suitable activating action such as by applying bursting pressure to the membrane. Those skilled in the art will recognize there are a variety of other ways that holes can be formed in hooks and elements within the spirit and scope of the present invention. For example, a hot knife or hot wire can horizontally cut across the top of conical projections.

Hollow elements on the thermoplastic web are filled using a variety of filling techniques. In the embodiment shown in FIG. 9, a supply conduit 168 introduces dispensable component 170 to the back of a sheet of hollow elements 104. Doctor blade 172 pressures dispensable component 170 into hollow elements 104 while removing excess. In the case of hollow volumes that are difficult to fill, vent passages are provided in hollow elements 104 to allow air to escape while hollow elements 104 are filled. In another example, the sheet is passed through a bath of fluid with the back of the hollow volumes of the formation directed upwardly, by which the volumes are filled.

Figure 9:
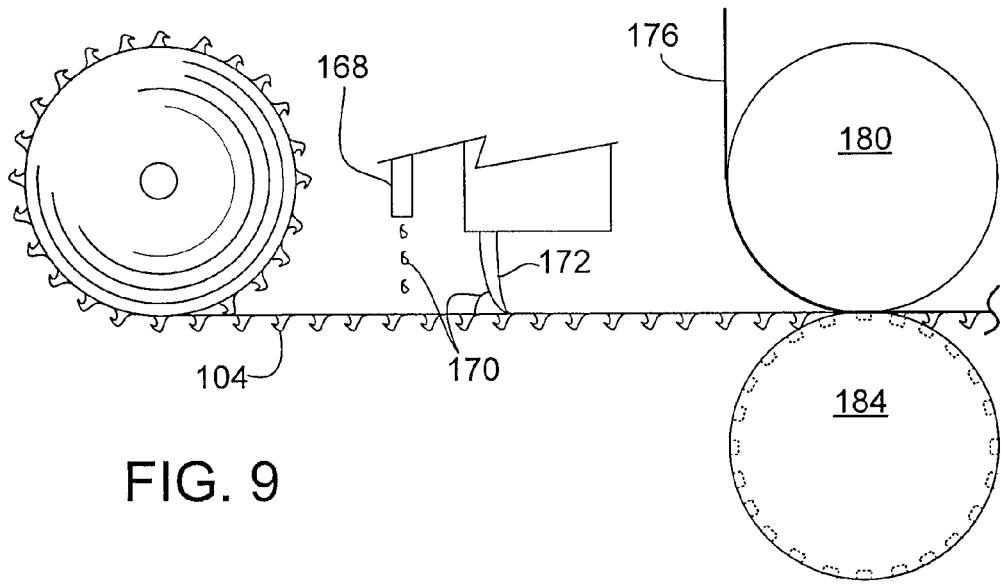
FIG. 9 is a schematic diagram of a filling and sealing apparatus.
Figure 9A:
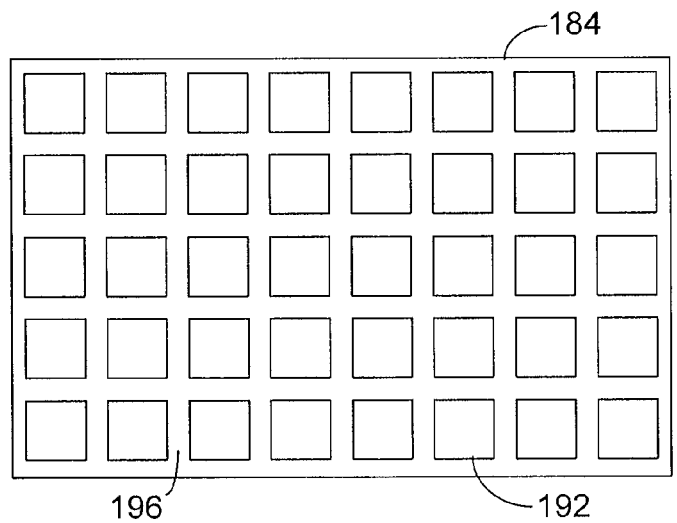
FIGS. 9A and 9B are, respectively, plan and side views of the developed surface of the pressure roll shown in FIG. 9.
Figure 9B:
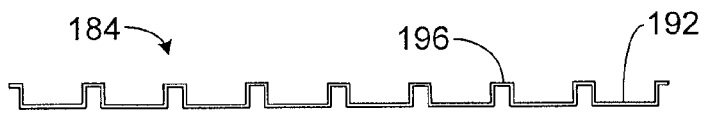

Following filling, provision is made to enclose the fluid. In certain embodiments, this is achieved by applying a backing member. Referring to FIG. 9, after filling, sheets of hollow elements 104 and backing material 176 are fed between laminating roll 180 and pressure roll 184. Hollow elements 104 are distributed in islands separated by regions of plain connecting material. As shown in FIGS. 9A and 9B, pressure roll 184 has surface recesses 192 between mating surfaces 196 that correspond, respectively, with islands of hooks 104 and bands of connecting material. Thus, backing material 176 is bonded at the plain bands to the sheet of hollow hooks using, for example heat and/or pressure, without compressing hooks 104. Examples of appropriate backing materials include but are not limited to a pressure-sensitive adhesive or a resin sheet compatible with the first resin.

Figure 9C:
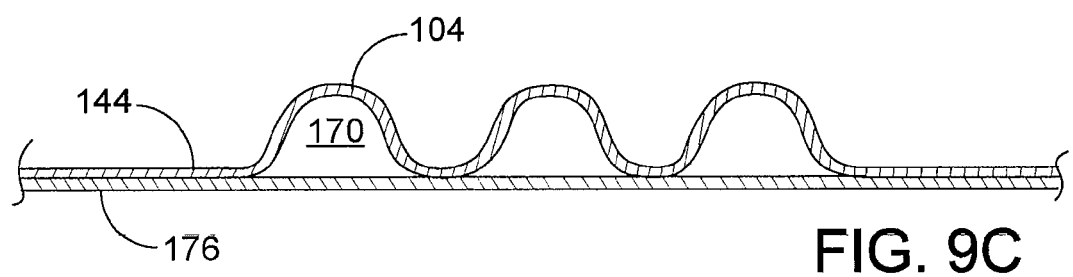
FIGS. 9C and 9D are, respectively, cross-section and plan views of a web product with filled elements as produced by the apparatus shown in FIGS. 6 and 9.
Figure 9D:
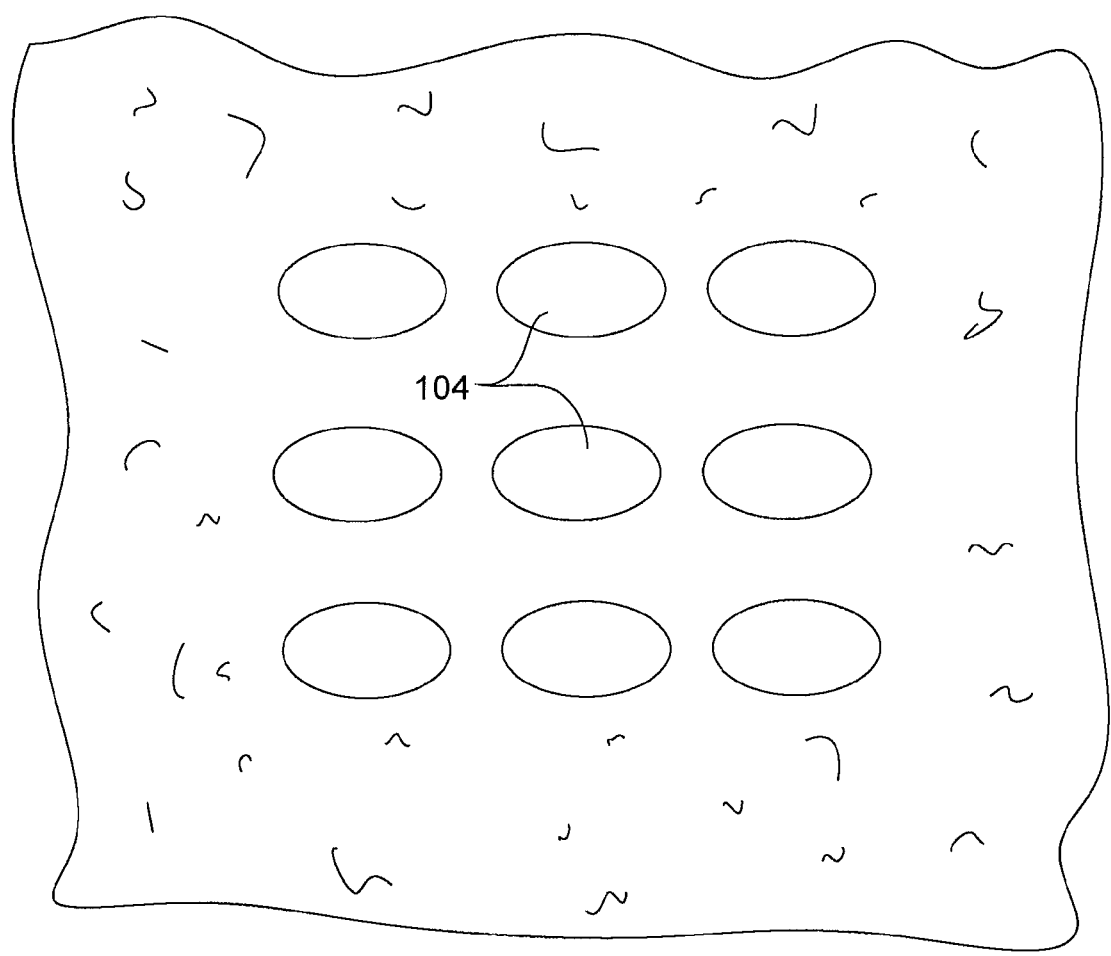

A sheet product produced by the process has regions of projections 104 separated by element-free regions as shown in FIGS. 9C and 9D. The resin layer 144 may not be bonded to backing material 176 in regions of elements 104. In this case, dispensable component 170 can migrate between elements 104. In alternative embodiments, other methods of sealing (such as, for example, ultrasonic sealing or thermoplastic sealing using, as the backing material 176, a preheated film that is very compatible with first resin 144) achieve bonding between first resin 144 and backing material 176 between individual elements 104 or small groups of elements so as to individually seal elements 104 or small groups. This is facilitated by providing a low density of elements 104 to minimize interference of filler with the seal to backing material 176.

In embodiments employed for dispensing, pressure acts to squeeze dispensable component from the hollow hooks. For this purpose, first resin is chosen to be flexible to produce hooks that are sufficiently deformable for the particular application. As discussed above, the dispensing exit for the dispensable component can be a hole or a weak spot that is opened by the application of pressure or other conditions of use. For example, a user can apply such pressure by pressing directly on a product to dispense a topical medicament. In another embodiment, some of the hooks of the tamper-evident fastener product described above dispense ink as they deform in response an applied peeling force of between about 0.1 and 2 pounds per inch width of the product.

Hole size and filler viscosity determine how easily dispensable component is dispensed and are chosen based on the characteristics and rate of flow desired for a particular application. In embodiments with holes, surface tension and viscosity of the fluid and the properties of the resin such as surface energy bias dispensable component to remain inside hollow elements until pressure is applied. In some embodiments, these may be sufficient to secure the fluid. In other cases, a membrane covers the dispensing holes, or a plugging material is employed. In embodiments with a weak spot, use of a suitable rupturable resin is appropriate. Alternatively, the tip of the hook may be treated to render it susceptible to opening.

Figure 10A:
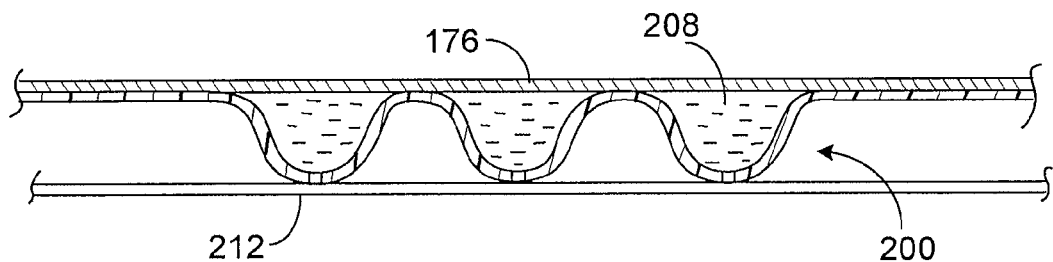
FIGS. 10A and 10B are cross-sections of a scent-filled web product for use in applications such as diapers, garbage can liners, and perfume samplers, respectively, before and after sealing tape is removed.
Figure 10B:
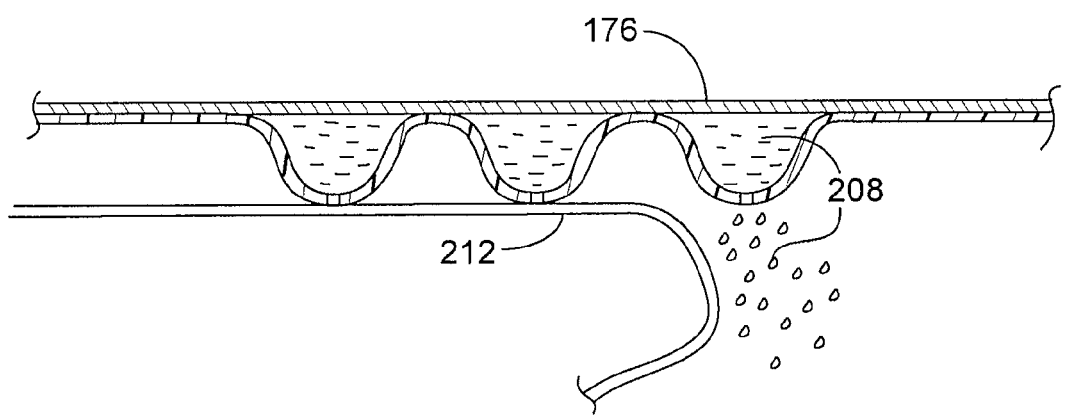

Hollow hooks and hollow dispensers of other forms are usable in a wide variety of applications. In FIG. 1, a tamper-evident fastener hook was shown. In another example, hollow hooks or dispensers are filled with other functional fluids. Referring to FIGS. 10A and 10B, dispensers 200 are filled with a scented fluid 208 prior to the holes being closed with a sealing tape 212 as shown in FIG. 10A. Such dispensers 200 are usable in products such as garbage bags and diapers where it is desirable to release a scent when the products are contacted during use. Sealing tape 212 also makes such dispensers useful for products such as scratch-and-sniff perfume sampler inserts for magazines where it is desirable to prevent inadvertent release of scented fluid 208. Removal of sealing tape 212 releases the scented fluid, see FIG. 10B.

Other appropriate fillers for hollow hooks and dispensers include but are not limited to suntan lotion, cosmetics, insect repellents, and medicines including topical anesthetics and antibiotics in fluid or powder form. Hollow hooks and hollow dispensers are also usable in feminine care products.

As has been indicated, appropriate characteristics for a dispensable component depend on the planned application and construction of the dispensing formations. However, in general, it is desirable that the dispensable component have a high viscosity in order to minimize leakage. Fillers with a viscosity of approximately 1,000 centipoises or higher are presently contemplated.

In some embodiments, stiff materials (e.g., rigid PVC, polyester polyethylene terephthalate, highly filled resins, or even moldable metal) can be processed in a roll molding apparatus for hook formation. Fastener products manufactured from stiff materials (e.g., materials with a flexural modulus greater than about 300,000, 500,000, or 750,000 pounds per square inch) can provide desirable high strength fastening properties (peel, shear, tension). However, it is difficult to process stiff materials in a roll molding apparatus with mold roll 108 made of metal because the material being molded into fastener hooks must be flexible to bend as the hooks are pulled from mold cavities 136. In a dual-layer process to form fastener hooks from stiff material, moldable stiff material is run in bottom layer 148 and a compressible material (e.g., sanoprene, low density polyethylene, urethane, or material with a compressive yield strength less than 20 MPa) is run in upper layer 144. Thus, as tension is exerted to remove the web of dual layer material from mold roll 108 fastener elements of the stiff material compress the top layer 144 as the adjacent layers 144, 148 are pulled from mold cavities 136. Upper and lower layers are subsequently separated.

Figure 4:
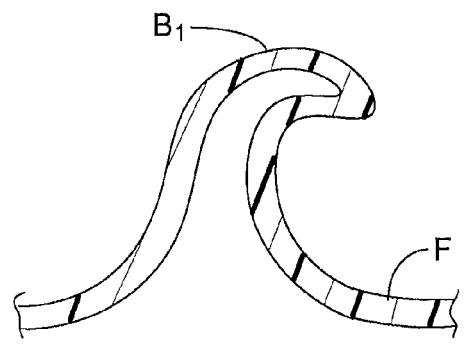
FIG. 4 is a cross-section of the upper layer of the sheet-form product of FIG. 2 after separation from the lower layer.
Figure 5:
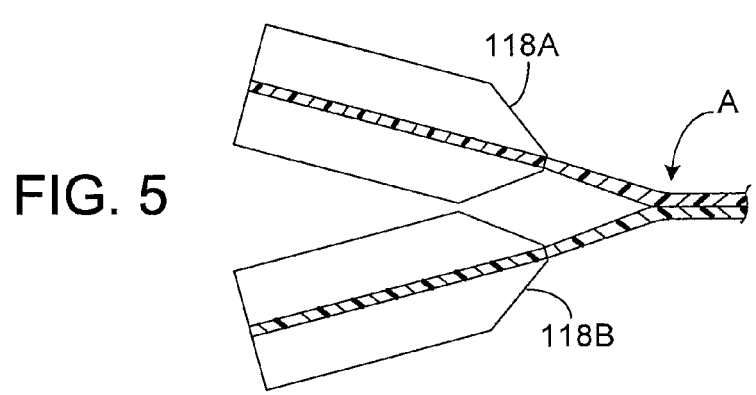
FIG. 5 is cross-section of two dies extruding two resins to form a single two-layer sheet.
Figure 11A:
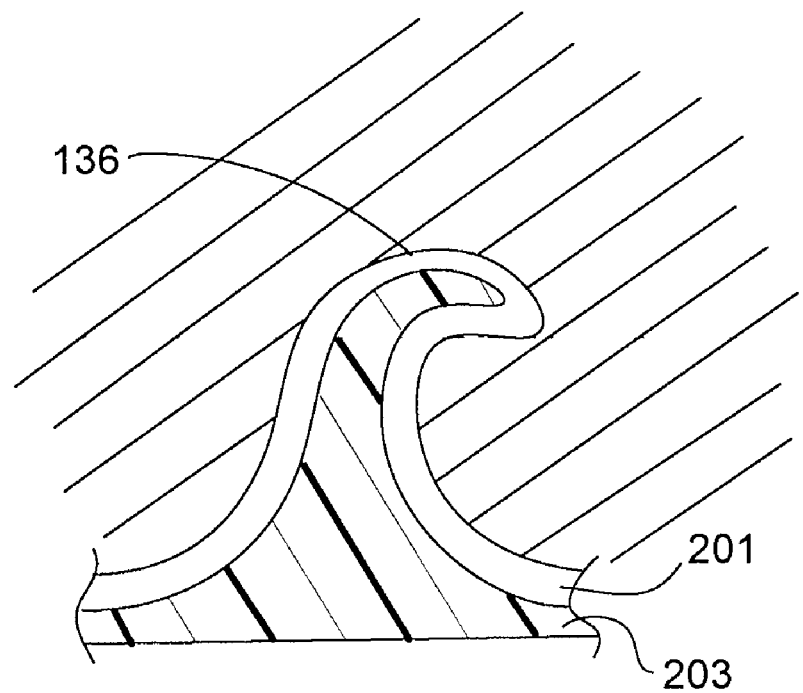
FIGS. 11A and 11B are cross-sections of an embodiment of a fastener hook.
Figure 11B:
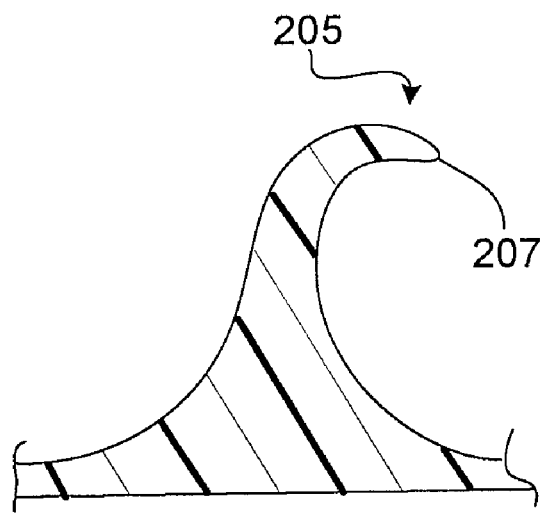

Similarly, in some embodiments, use of a compressible sacrificial layer can enable production of hook shapes that would be otherwise difficult or impossible to produce through a roll molding process. For example, referring to FIGS. 11A and 11B, a hook 205 with a steep long crook 207 would be difficult to remove from mold cavity 136 if made from a material with a high enough flexural modulus to provide the hook with sufficient strength properties to function as a fastener element. However, sacrificial layer 201 can be formed of a material a compressible material that would allow a lower layer 203, formed of a stiffer material, to compress into the sacrificial layer as hook 205 is removed from mold cavity 136. The shape of hook shape 205 can provide improved strength properties (peel, shear, tension) relative to the fastener elements as shown in FIGS. 2-4.

Similarly, in some embodiments, fastener hooks are formed with crooks facing in a substantially cross-machine direction as disclosed in U.S. Pat. No. 6,224,807, the entire contents of which are incorporated herein by reference. In this context, machine direction refers to the direction substantially aligned with the rotation of the mold roll and cross-machine direction is the direction along the axis of the mold roll and substantially perpendicular to the machine direction. Cross-machine direction facing hooks tend to have a twisted crook because the hooks face cross-machine direction but are pulled out in the machine direction. This tendency can be reduced through the use of a compressible sacrificial layer, as discussed above, which would allow cross-machine direction facing cavities to be filled with resin and the resulting hook be removed from the mold cavity with reduced twisting of crook. The sacrificial layer would take the brunt of the twist, and the lower layer would partially compress the upper layer during removal from the mold cavity, thus reducing the crook twist.

Figure 12A:
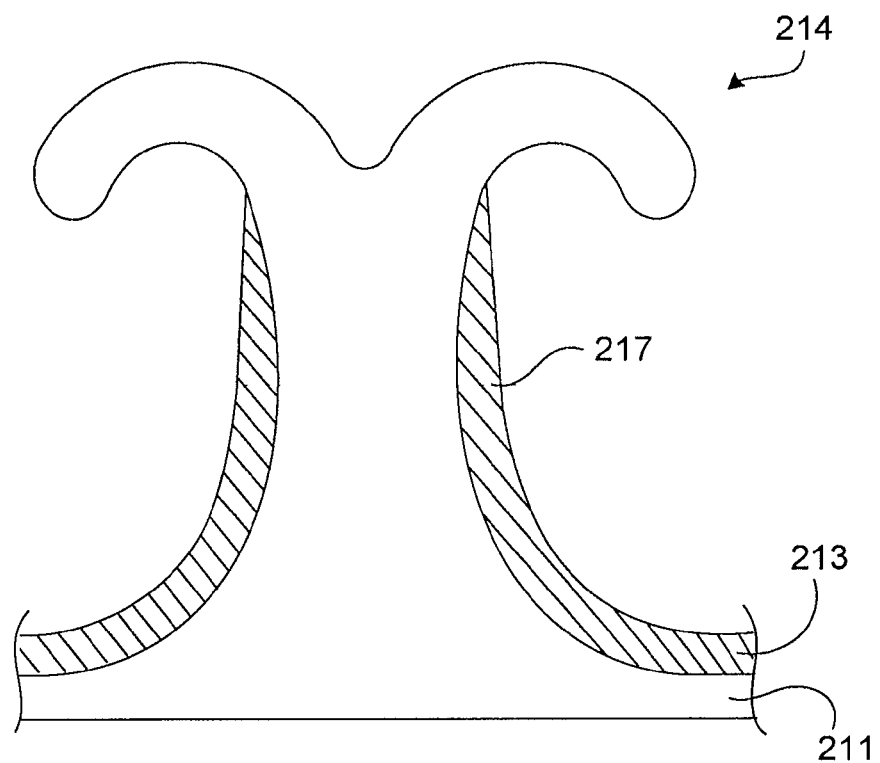
FIGS. 12A and 12B are cross-sections of an embodiment of a fastener hook.
Figure 12B:
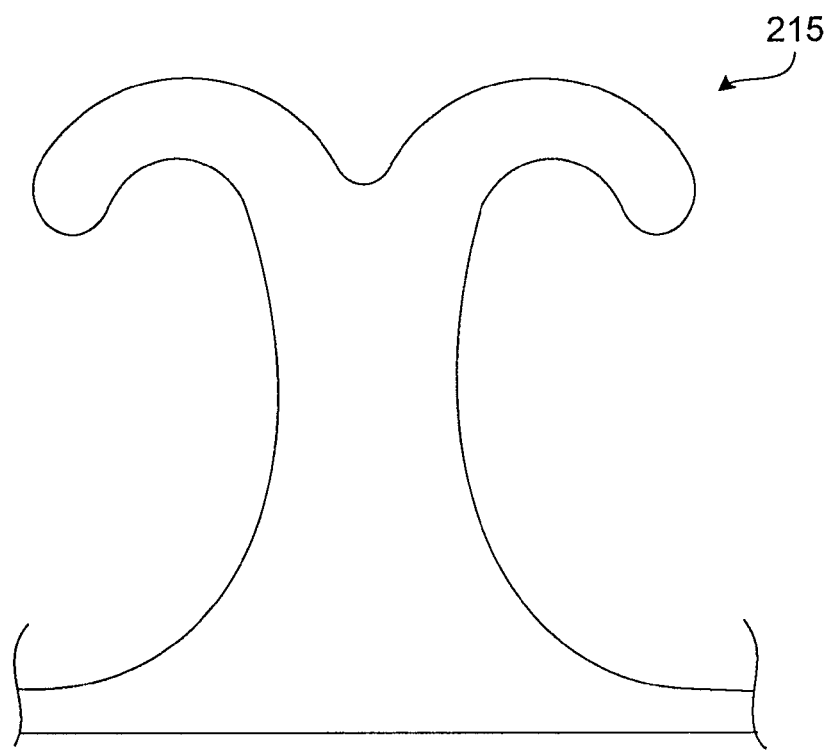

Referring to FIGS. 12A and 12B, in some embodiments, material (e.g., polymer resins) for two layers 211, 213 can be chosen and processed such that the bottom layer 211 extends through the top layer 213. For example, a fractional melt flow resin can be run as top layer 213 and frozen off quickly such that bottom layer 211 is forced through the top layer to complete the cavity fill, such that the two layers together form hooks 214 with stems 217 whose thickness is sufficient that the stems can be used to pull the hooks out of a mold cavity. Top layer 213 is then removed, leaving the bottom layer as a hook 215 with a thin stem 217 but a large head 219. If the resulting hook 215 was molded in final form in a fixed mold cavity without second layer 213, the hook would be "mold-locked" and would not be removable from the cavity. Large-headed hooks 215 provide good strength properties (peel, shear, tension), at least in part because the relatively flexible stems allow the hook to bend to follow the load, the extra deflection increasing the number of engaged hooks that develop loading at any given time.

Figure 13A:
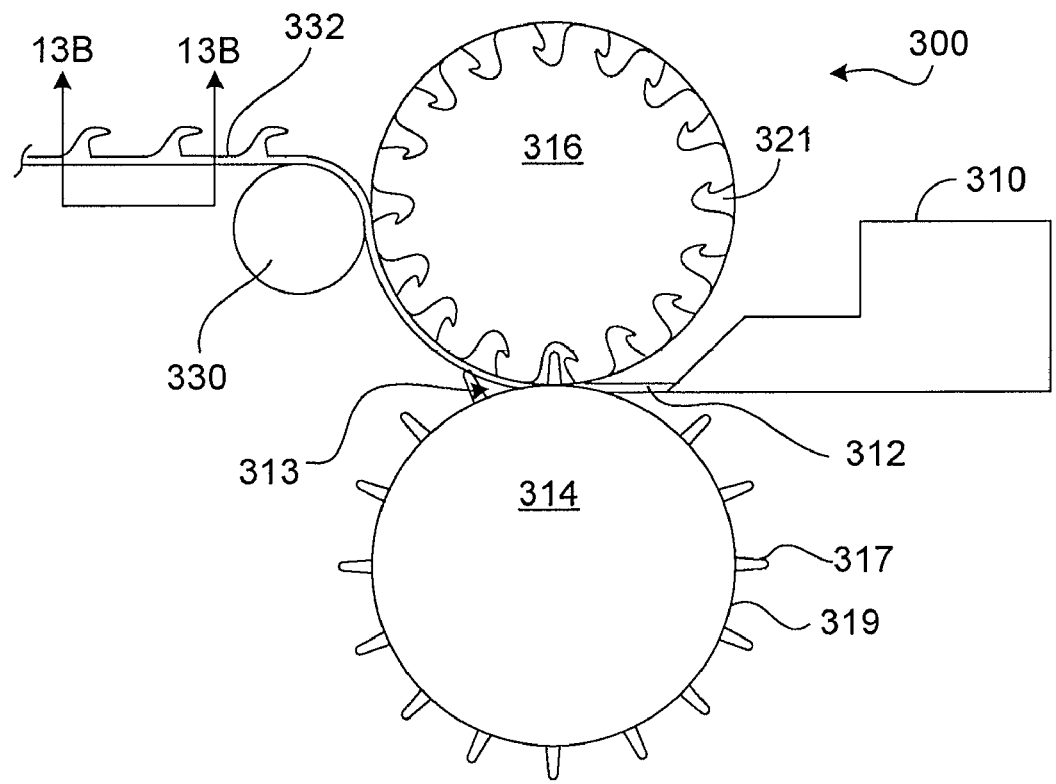
FIGS. 13A and 13B are, respectively, an embodiment of system for molding hollow fastener elements and an embodiment of the resulting fastener hook.
Figure 13B:
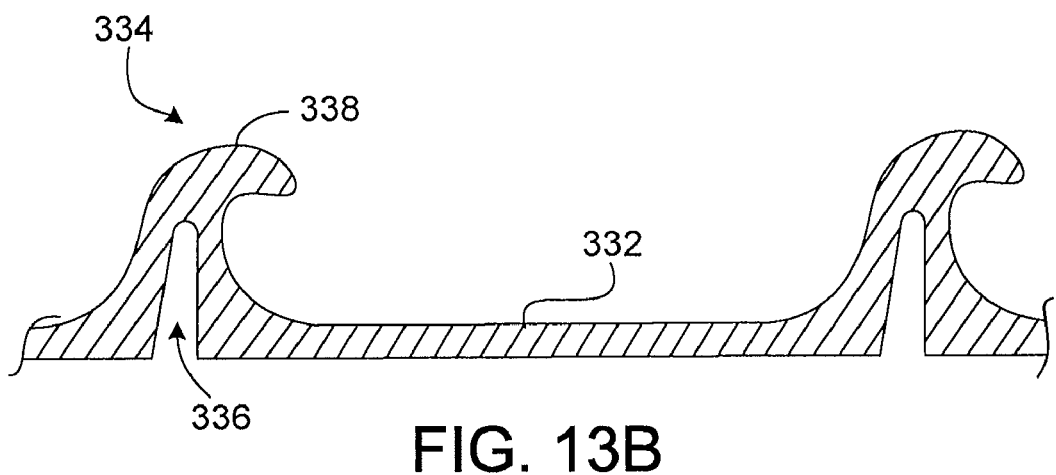

Other approaches can also be used to form hollow elements. Referring to FIGS. 13A and 13B, a system 300 includes an extruder 310 which feeds molten resin 312 into nip 313. Nip 313 is defined between a pressure roll 314 and a mold roll 316. Pressure roll 314 includes protrusions 317 extending outward from a peripheral surface 319 of the pressure roll. Protrusions 317 are sized to fit with mold cavities 321 defined in mold roll 316. Pressure roll 314 and mold roll 316 are oriented such that protrusions 317 align with mold cavities 321. As molten resin 312 enters nip 313, protrusions 317 displace some of the resin that would otherwise be present in mold cavities 321. Takeoff roll 330 and removes resin 312 from mold roll 316 after the resin has solidified sufficiently to apply removal tension. Resulting fastener web 332 includes hooks 334 with interior cavities 336 and solid crooks 338. Interior cavities 336 provide hooks 334 with increased flexibility for improved engagement while crooks 338 provide hooks 334 with good strength properties.

A number of embodiments have been described. Nevertheless, it will be understood that various modifications may be made without departing from the spirit and scope of the invention. For example, in some embodiments, a dispensable component is applied discretely in the vicinity of hollow elements using a jetting process analogous to the processes used by ink-jet printers.

Accordingly, other embodiments are within the scope of the following claims.

What is claimed is:

1. A method of forming a sheet-form product, the method comprising:
    providing a forming surface having a multiplicity of inwardly extending forming cavities;
    forming a multi-layer sheet in the interior of which is a parting surface defined by resin materials of limited compatibility, a first resin of the sheet lying on one side of the parting surface and a second resin lying on an opposite side of the parting surface, the parting surface having peelable tensile strength;
    pressing the multi-layer sheet against the forming surface to cause the first resin and the second resin of the multi-layer sheet to substantially conform to and fill the cavities of the forming surface; and
    peeling the multi-layer sheet apart at the parting surface, whereby material directly engaging the forming surface defines a sheet-form member having a multiplicity of hollow formations.

2. The method of claim 1 in which the forming cavities define at least stems for fastener elements.

3. The method of claim 2 wherein the forming cavities define cylindrical formations.

4. The method of claim 2 wherein the forming cavities define loop engageable formations.

5. The method of claim 4 wherein the loop engageable formations are molded hooks.

6. The method of claim 1 wherein forming a multi-layer sheet comprises continuously introducing a first molten thermoplastic and a second molten thermoplastic into a gap defined adjacent to the forming surface.

7. The method of claim 1 further comprising, forming a dispensing hole in the hollow formations.

8. The method of claim 7 wherein forming a dispensing hole comprises laser radiating the hollow formations to burn through the sheet-form member.

9. The method of claim 7 wherein forming a dispensing hole comprises mechanically piercing the hollow formations.

10. The method of claim 1 wherein mold pins extend into the forming cavities from a body of the forming surface.

11. The method of claim 1 further comprising, weakening a discrete area of the hollow formations.

12. The method of claim 11 wherein weakening comprises laser radiating the hollow formations for a period of time chosen to decrease the structural strength of a discrete area of the hollow formations without burning through the sheet-form member.

13. The method of claim 1 further comprising filling the hollow formations with a flowable substance.

14. The method of claim 13 further comprising, after filling, bonding a backing layer to the sheet-form member to form a multiplicity of substantially enclosed chambers.

15. The method of claim 14 wherein the flowable substance comprises a component that volatilizes when exposed to the atmosphere.

16. The method of claim 13 further comprising choosing the flowable substance from a group including: a medicament appropriate for topical application; an antibiotic; an analgesic; components that reduce transmission of ultraviolet radiation; and components that repel insects.

17. A method of forming a sheet form product, the method comprising:
    forming a multi-layer sheet having a first resin layer forming a first broad surface of the multi-layer sheet;

pressing the multi-layer sheet against a forming surface with the first resin layer contacting the forming surface such that the first resin layer and an additional layer of the multi-layer sheet substantially conform to and fill a multiplicity of inwardly extending forming cavities in the forming surface and such that the first resin layer separates remaining portions of the multi-layer sheet from the forming surface;

removing the multi-layer sheet from the forming surface; and removing the first resin layer from the remaining portions of the multi-layer sheet, the remaining portions of the multi-layer sheet defining a member have stems of fasteners elements integrally molded with and extending from a sheet-form base.

18. The method of claim 17 wherein the remaining portions comprise additives.

19. The method of claim 18 wherein the additives comprise materials, such as titanium dioxide or calcium carbonate, that increase the rate of accumulation of contaminating material on the surfaces the resin and additives contact and the method further comprises sizing a thickness of the first layer to limit contact between the forming surface and the remaining portions.

20. The method of claim 18 wherein the additives comprise materials that increase abrasive characteristics of the remaining portions and the method further comprises sizing a thickness of the first layer to reduce wear on the forming surface from the remaining portions.

21. The method of claim 17 further comprises sizing a thickness of the first layer based on sizes of irregularities in the forming surface.

22. The method of claim 17 further comprising selecting materials for the first layer that have a first flexural modulus and materials for the remaining portions that have a second flexural modulus such that the second flexural modulus is greater than the first flexural modulus.

23. The method of claim 22 wherein the second flexural modulus is greater than 300,000 pounds per square inch.

24. The method of claim 23 wherein the second flexural modulus is greater than 500,000 pounds per square inch.

25. The method of claim 24 wherein the second flexural modulus is greater than 750,000 pounds per square inch.

26. The method of claim 22 wherein removing the multi-layer sheet from the forming surface comprises compressing the first layer between the forming surface and remaining portions.

27. The method of claim 22 further comprising forcing the remaining portions through the first layer.

* * * * *